(12) United States Patent
Sukovic et al.

(10) Patent No.: US 8,303,181 B2
(45) Date of Patent: Nov. 6, 2012

(54) INTRAOPERATIVE COLLAPSABLE CT IMAGING SYSTEM

(75) Inventors: Predrag Sukovic, Birmingham, MI (US); Neal Clinthorne, Ann Arbor, MI (US); Nathaniel Bair, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 1392 days.

(21) Appl. No.: 10/914,500

(22) Filed: Aug. 9, 2004

(65) Prior Publication Data

US 2005/0054915 A1    Mar. 10, 2005

Related U.S. Application Data

(60) Provisional application No. 60/493,195, filed on Aug. 7, 2003.

(51) Int. Cl.
*A61B 6/00* (2006.01)

(52) U.S. Cl. ............. 378/197; 378/4; 378/198; 378/205

(58) Field of Classification Search .................. 600/407, 600/425
See application file for complete search history.

(56) References Cited

U.S. PATENT DOCUMENTS

| | | | |
|---|---|---|---|
| 4,775,994 A | 10/1988 | Kranvogel | |
| 5,515,416 A * | 5/1996 | Siczek et al. | 378/197 |
| 6,079,876 A * | 6/2000 | Schuetz | 378/205 |
| 6,120,180 A | 9/2000 | Graumann | |
| 6,203,196 B1 * | 3/2001 | Meyer et al. | 378/197 |
| 6,435,715 B1 * | 8/2002 | Betz et al. | 378/197 |
| 6,496,558 B2 * | 12/2002 | Graumann | 378/39 |
| 6,574,493 B2 | 6/2003 | Rasche et al. | |
| 6,577,889 B2 * | 6/2003 | Ichihashi | 600/425 |
| 6,619,840 B2 * | 9/2003 | Rasche et al. | 378/197 |
| 6,666,579 B2 * | 12/2003 | Jensen | 378/197 |
| 6,725,080 B2 * | 4/2004 | Melkent et al. | 600/424 |
| 6,869,217 B2 * | 3/2005 | Rasche et al. | 378/197 |

(Continued)

FOREIGN PATENT DOCUMENTS

FR    2 645 007    10/1990

OTHER PUBLICATIONS

International Search Report, Nov. 18, 2004.

*Primary Examiner* — Jacqueline Cheng
(74) *Attorney, Agent, or Firm* — Carlson, Gaskey & Olds, P.C.

(57) ABSTRACT

An imaging system includes a source and a detector that can be quickly and easily moved out of the way after scanning. During scanning, the actual paths that the source and detector travel are tracked, such as by an associated surgical navigation system tracking system. The actual locations of the source and detector during each x-ray image are used in the image reconstruction algorithm. Since the actual locations are used in the algorithm, the locations do not have to be as precisely controlled. In one embodiment, the source and detector are mounted proximate outer ends of first and second c-arm sections. The first and second c-arm sections are extendable to form a complete c-arm and retractable to a collapsed position when not in use. In the disclosed embodiment, the c-arm sections are mounted to a base or carriage under the patient support surface (such as the surgical table).

14 Claims, 5 Drawing Sheets

U.S. PATENT DOCUMENTS

| | | | |
|---|---|---|---|
| 6,920,347 B2 * | 7/2005 | Simon et al. | 600/424 |
| 7,609,808 B2 * | 10/2009 | Tornai et al. | 378/63 |
| 2002/0065461 A1 * | 5/2002 | Cosman | 600/426 |
| 2003/0235266 A1 | 12/2003 | Gregerson et al. | |
| 2004/0013225 A1 | 1/2004 | Gregerson et al. | |
| 2004/0013239 A1 | 1/2004 | Gregerson et al. | |
| 2004/0022350 A1 | 2/2004 | Gregerson et al. | |

* cited by examiner

INTRAOPERATIVE COLLAPSABLE CT IMAGING SYSTEM

This application claims priority to U.S. Provisional Application Ser. No. 60/493,195, filed Aug. 7, 2003.

BACKGROUND OF THE INVENTION

Image guided surgery is becoming more common, especially in the areas of inter-cranial surgery. Systems are utilized to take data gathered from pre-operative scans by MRI, CT scanners, ultrasounds, or the like. The data is used to generate a three-dimensional image to guide a surgeon during an operation. Often this includes some method for tracking an instrument location with respect to the image displayed by the system. Generally, the image is registered relative to locators attached to the patient. Then, the position and orientation of the surgical instruments is registered and tracked relative to the image and the patient so that the location and orientation of the instruments relative to the image is continuously displayed while the surgeon performs the surgery.

The problem with using the pre-operative image is that the object selected may have shifted between the time the pre-operative image was taken and the time of surgery. This is especially true once surgery has begun and the shape of the intercranial cavity changes as the surgeon gains access. Changes in the pre-operative image and the actual surgical subject introduce variations into the surgical process. In matters like intercranial surgery the tolerance for variations is low, thus even small changes between the image and actual subject may cause problems and make the surgery less effective. To solve this problem additional images may be taken during surgery to update the previously received information. However, selecting the area to be scanned, setting up the intra-surgery scanner, and performing the scan require movement of bulky equipment and surgery must be stopped to set up the equipment properly and perform the scan. In addition it is difficult to move the equipment to the desired area to be scanned thus increasing the time and effort required to update the image properly. Thus, because of the time and effort required, intraoperative scans are generally not used.

SUMMARY OF THE INVENTION

The present invention provides an imaging system that is particularly advantageous for intraoperative use, although it may be used anywhere that space and easy setup is important. Generally, the imaging system includes a source and a detector that can be quickly and easily moved out of the way after scanning. Since much of the bulk of the known CT scanners comes from the structure that moves the source and detector along precisely controlled, predetermined paths, one way that the imaging system of the present invention reduces its size is by eliminating the requirement for such precisely controlled, predetermined paths. Instead, the actual paths that the source and detector travel are tracked, such as by the surgical navigation system tracking system. The actual locations of the source and detector during each x-ray image are used in the image reconstruction algorithm. Since the actual locations are used in the algorithm, the locations do not have to be as precisely controlled.

In one embodiment, the source and detector are mounted on opposite ends of a collapsible c-arm. The source is mounted at an outer end of a first c-arm section and the detector is mounted at an outer end of a second c-arm section. The first and second c-arm sections are extendable to form a complete c-arm and retractable to a collapsed position when not in use. In the disclosed embodiment, the c-arm sections are mounted to a base or carriage under the patient support surface (such as the surgical table). The carriage includes a motor for driving the c-arm rotatably about the patient support surface. The carriage is also movable longitudinally under the patient support surface, so that any desired portion of the patient can be scanned. Other embodiments and variations are also disclosed.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENTS

Figure 1:
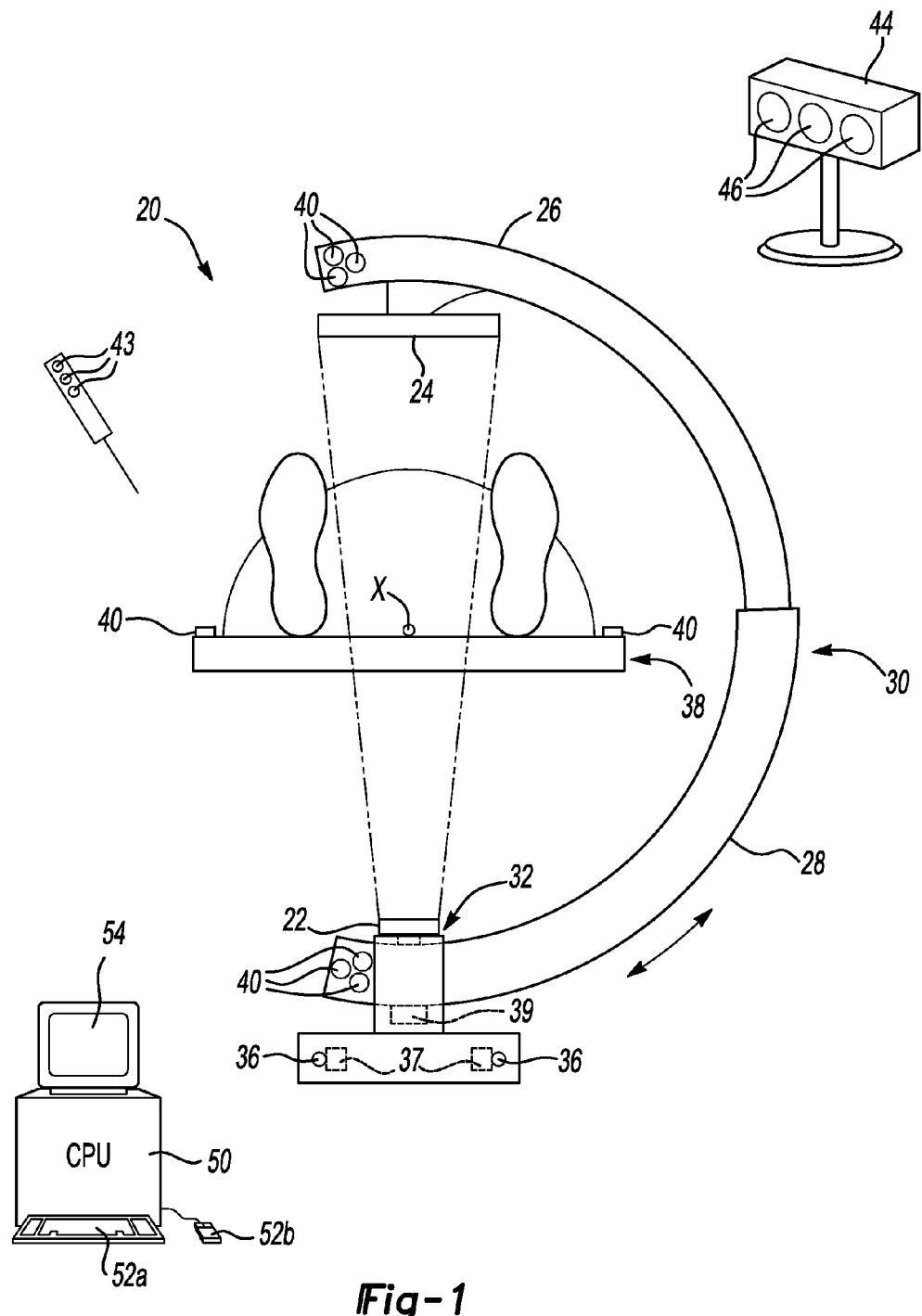
FIG. 1 is an end view of imaging system according to a first embodiment of the present invention, showing the c-arm in a first position.
Figure 2:
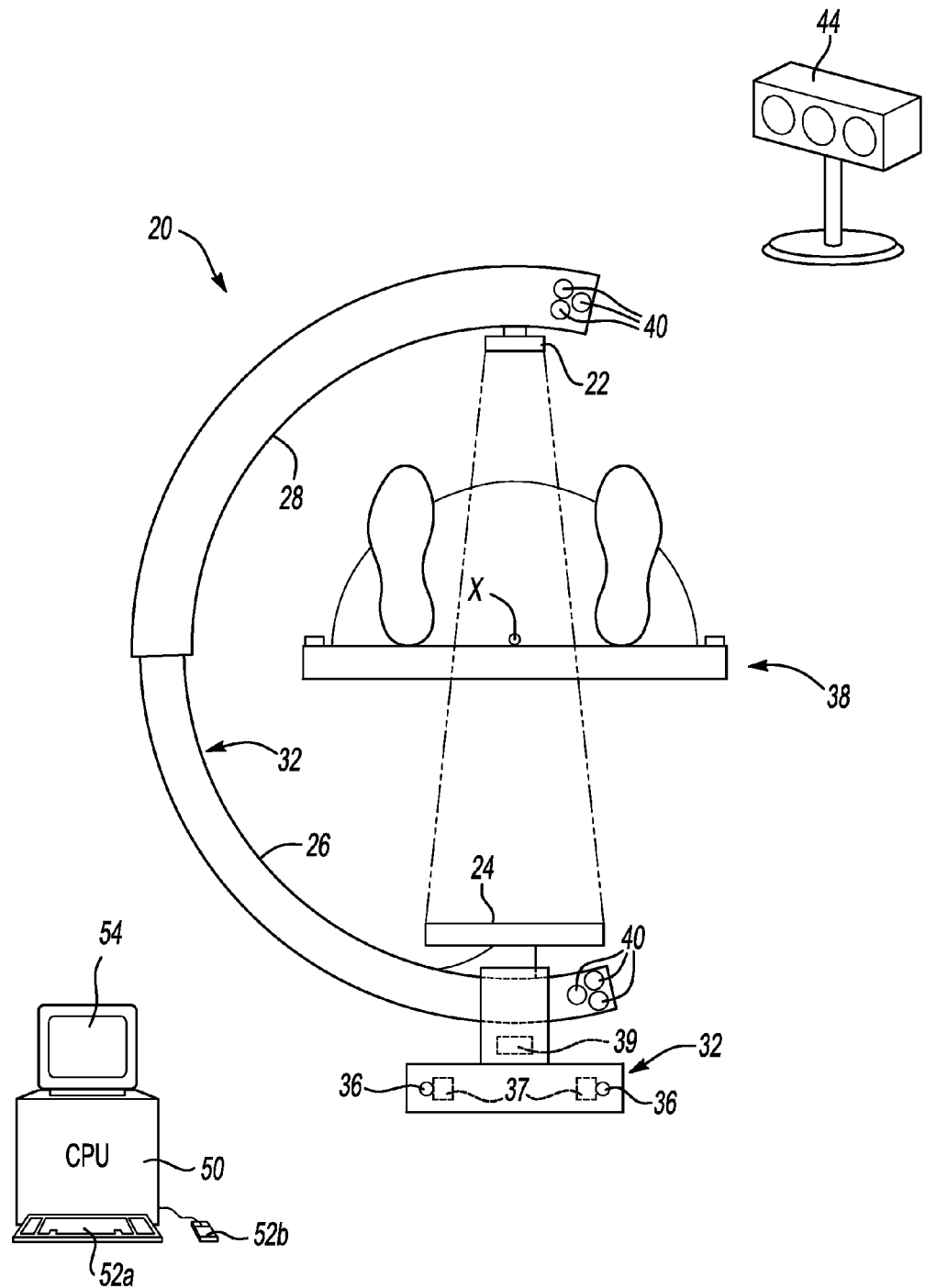
FIG. 2 shows the c-arm in a second position.

A first embodiment of an intraoperative imaging system 20 according to the present invention is shown in FIGS. 1-4. The imaging system 20 is particularly useful for image-guided surgery or other applications where intra-operative imaging would be desired. Although applicable for other types of imaging systems, the present invention will be described with respect to an intra-operative CT scanning system 20 for illustrative purposes. Referring to FIG. 1, the CT scanning system 20 includes a source 22 and detector 24 mounted at outer ends of a first c-arm section 26 and a second c-arm section 28, respectively. The source 22 may be a cone-beam x-ray source 22. The detector 24 may be a flat panel detector 24 having a converter for converting x-rays into light which is detected by an array of photodetectors.

The first and second c-arm sections 26, 28 are slidably connected to one another, such that first c-arm section 26 slides telescopes within the second c-arm section 28. The first and second c-arm sections 26, 28 can be extended to the position shown in FIG. 1, where they form a complete c-arm 30, thereby positioning the centers of the source 22 and detector 24 180 degrees apart.

The c-arm 30 is also preferably slidably mounted within a carriage 32, such that the c-arm 30 can be rotated approximately slightly more than 180 degrees generally about an axis x, substantially centered within the c-arm 30 and positioned substantially between the source 22 and detector 24. The carriage 32 is also slidably mounted on rails 36 such that the carriage 32 and c-arm 30 can translate along the x-axis. One or more motors 37 control the position and motion of the carriage 32 on the rails 36. The carriage 32 and/or the rails 36 may be part of (or simply placed below) an operating table 38. The carriage 32 preferably includes a motor 39 engaging the c-arm 30 to drive the c-arm 30 about the x-axis in a controlled manner.

The patient and/or the table 38 may include fiducials or locators 40 that are detectable on the CT images, so that the position and orientation of the surgeon's tools 43 can subsequently be determined relative to the three-dimensional image by an image-guided surgery tracking system 44 according to known image-guided surgery techniques. Several types of suitable tracking systems 44 are known.

The tracking system 44 may include sensors 46, which may be CCDs that optically detect the locators 40, RF receivers that receive wireless signals from the locators 40 or lasers that measure distance to each of the locators 40. Other known types of tracking systems 44 could also be utilized. The present invention is independent of the specific type of tracking system 44 used. Additionally, the c-arm sections 26, 28 may include locators 40 such that their position and orientation can be determined relative to the image-guided surgery tracking system 44 and relative to the table 38.

If the c-arm sections 26, 28 include locators 40, the ability of the c-arm 30 to keep the source 22 and detector 24 at precisely fixed locations relative to one another becomes less important. Since the tracking system 44 determines the location of the c-arm sections 26, 28 (and thus, the source 22 and detector 24), at each position at which an x-ray image is taken, these coordinates can be used in the reconstruction algorithm, in which the multiple x-ray images are used to construct a 3D image of the scanned area. The data in each x-ray image may be corrected or otherwise offset prior to reconstruction in order to take into account the true position of the source 22 and detector 24, which may not travel along a perfect arc at precise, equal intervals due to the fact that they are mounted on a c-arm 30, especially a c-arm 30 that is formed in sections. Alternatively, the locations of the source 22 and detector 24 at which each x-ray image was taken may be factored directly into the reconstruction algorithm, i.e. rather than trying to "correct" the data back to ideal source and detector locations prior to reconstruction, using the actual locations of the source and detector in the reconstruction algorithm. Also, for the same reasons, it is not important that the c-arm 30 actually rotate about a single axis, but it should generally rotate about the area of interest in the patient to be scanned, which may be an area in or near the interior of the arc of the c-arm 30.

A computer 50 has a processor, memory and storage and is suitably programmed to perform the functions described herein. The computer 50 may include a keyboard 52a and a mouse 52b as user input devices and a display 54. The computer 50 controls the function and operation of the devices in the manner described herein. The computer 50 also receives the x-ray images from the detector 22 and reconstructs a 3D image from the x-ray images using suitable techniques. The computer 50 controls the motor 39 to move the c-arm 30 through the carriage 32 about the x-axis while the x-ray images are taken at selected intervals. The computer 50 also receives the data from the tracking system 44 and corrects or offsets the data received from the detector 24 by the data indicating the positions of the data 22 and detector 22 in the reconstruction algorithm.

The c-arm 30 is rotated about the x-axis by the motor 39 in the carriage 32 as controlled by the computer 50. The c-arm 30 is rotatable about the x-axis approximately a little greater than 180 degrees to the position shown in FIG. 2, such that a complete scan of the patient can be taken.

Figure 3:
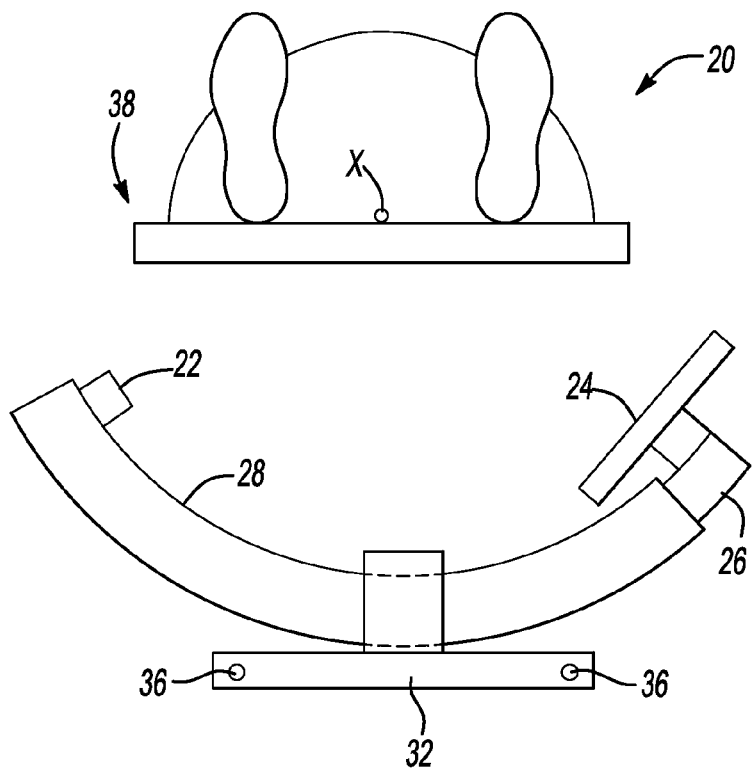
FIG. 3 shows the c-arm in a collapsed position.
Figure 4:
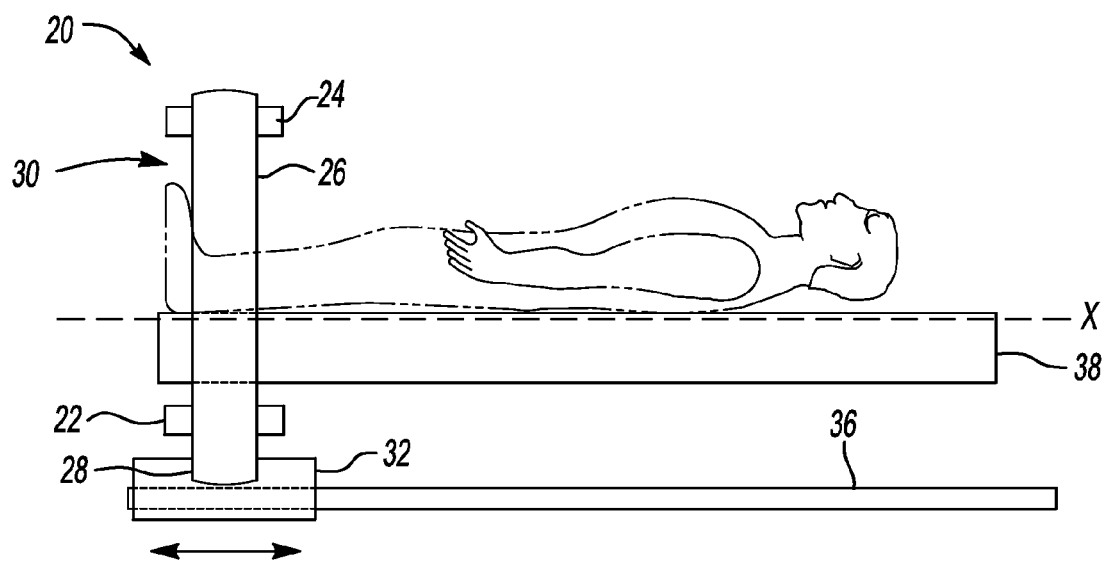
FIG. 4 is a side view of the imaging system of FIG. 1 in use.

In use, the imaging system 20 may initially be stored below the operating table 38 prior to use as shown in FIG. 3. In FIG. 3, the c-arm sections 26, 28 are retracted to a position below the table 38 out of the way of the surgeons and assistants. When a pre-operative or intra-operative image is desired, the c-arm sections 26, 28 are extended to the position shown in FIGS. 1-2 and the imaging process is initiated, depending on the type of image desired. If a CT scan is required, the carriage 32 is moved along the rails to the desired portion of the patient's body, as shown in FIG. 4. The source 32 and detector 24 are then activated to produce a plurality of x-ray images of the desired portion of the patient's body. The c-arm 30 is rotated about the x-axis by computer-controlled motors in the carriage 32 as the source 32 and detector 34 take x-ray images at spaced intervals sufficient to create or update a three-dimensional image of the portion of the patient's body. The tracking system 44 repeatedly determines the positions of the source 22 and detector 24, which are correlated to the x-ray images sent by the detector 24 to the computer 50. The computer-controlled motors 37 may also move the carriage 32 along the rails 36 during rotation of the c-arm 30, in order to produce a "rectified helical" scan (not a true helix, since the c-arm does not perform a complete orbit, but rotatably oscillates between the positions of FIGS. 1 and 2).

After scanning, the computer 50 reconstructs the 3D image of the portion of the patient based upon the x-ray images and positions of the source 22 and detector 24 at which each image was taken. The reconstructed image is then displayed on the display 54. The c-arm 30 is collapsed again and moved out of the way under the table 38 so that surgery can begin (in the case of a preoperative scan) or continue (in the case of an intraoperative scan). Those of skill in the art would be able to develop the reconstruction algorithms described herein based upon the particular implementation chosen.

Figure 5:
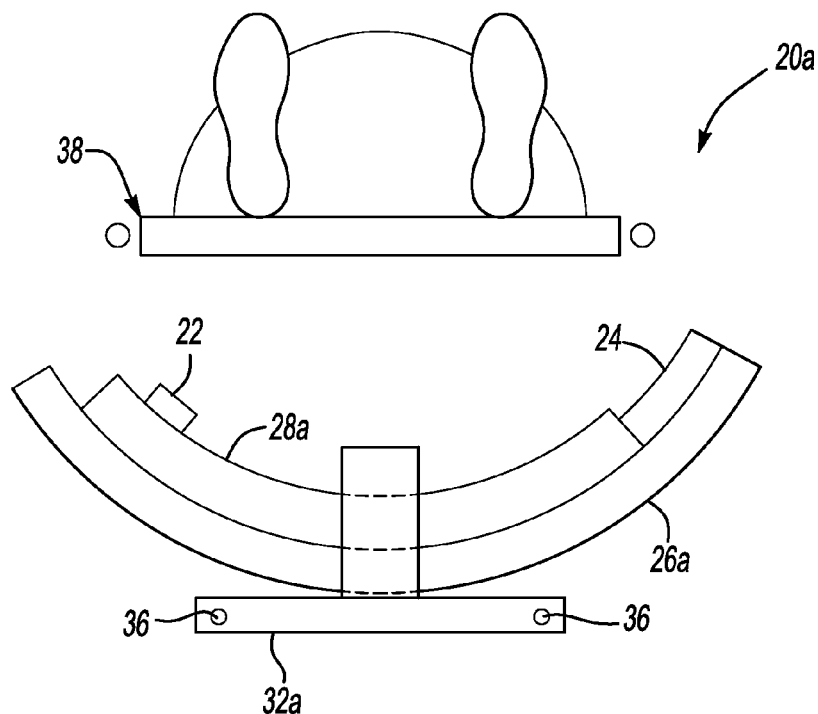
FIG. 5 is an end view of an imaging system according to a second embodiment of the present invention.

A second embodiment of the system 20a is shown in FIG. 5. In FIG. 5, the c-arm section 28a is slidably mounted along the inner arc surface of the c-arm section 26a. The c-arm sections 26a, 28a are shown in the collapsed position in FIG. 5. Otherwise, the operation is as described above.

Figure 6:
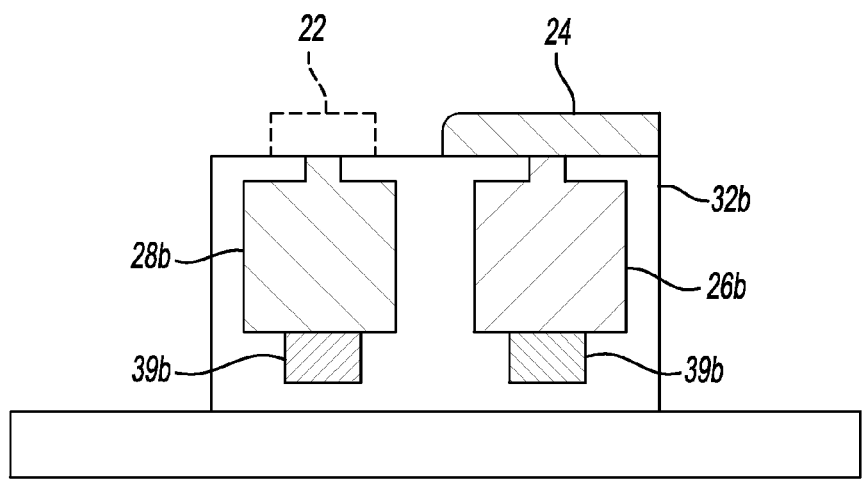
FIG. 6 is a sectional view through the carriage of a third embodiment of the present invention.

A third embodiment is shown in FIG. 6, which is a section view through the carriage 32b. In this embodiment, the c-arm sections 26b, 28b are separately supported in the carriage 32b, with separate motors 39b driving each about the axis during scanning. Although the source 22 and detector 24 are offset slightly along the x-axis, they can be tilted slightly to accommodate this offset.

Figure 7:
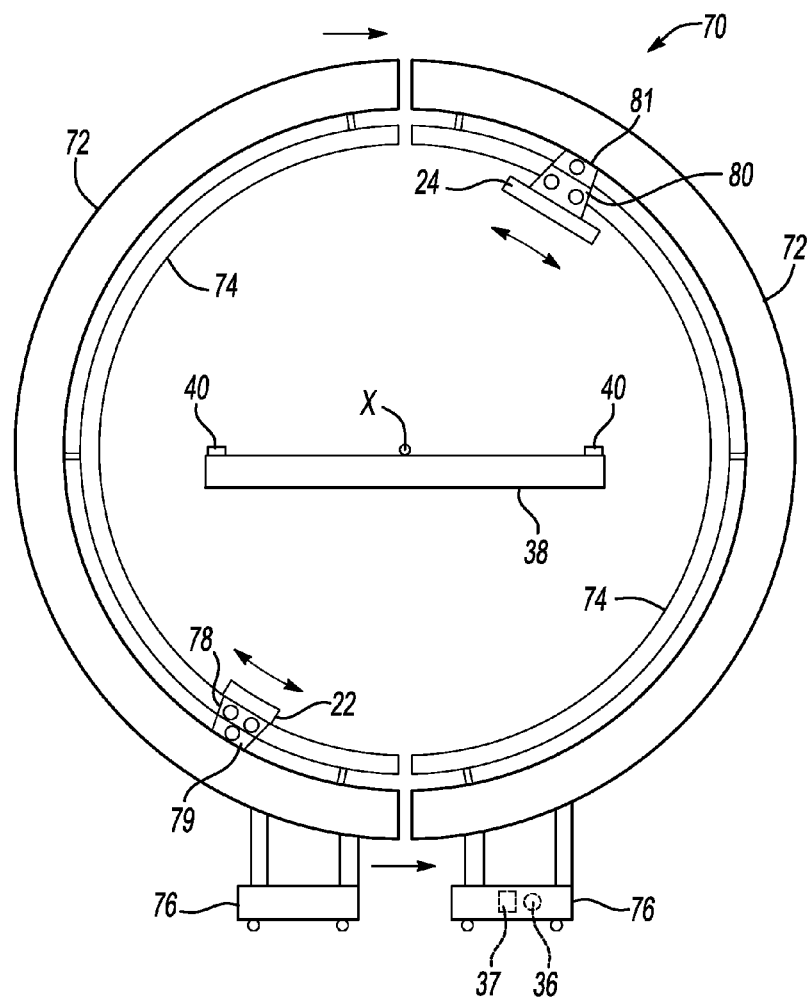
FIG. 7 is an end view of a fourth embodiment of the present invention.

An imaging system 70 according to a fourth embodiment of the present invention is shown in FIG. 7. The imaging system 70 comprises a pair of c-arm halves 72 each having a rail 74 mounted on its inner circumference. Each c-arm half 72 is mounted on a movable base 76, such that they can be moved together for scanning and away from one another after scanning. At least one of the bases 76 is mounted to the rail 36 (also shown in FIG. 4) and includes the motor 37 for translating the system 70 along the rail 36 as described above. The c-arm halves 72 and rails 74 are attachable to one another to form an outer ring from c-arm halves 72 and an annular inner rail from rails 74. The source 22 is mounted to a computer-controlled carriage 78 having a motor 79. The detector 24 is mounted to a separate, independently controlled, motorized carriage 80 having a motor 81. The carriages 78, 80 each include a plurality of the locators 40 (described above) for use with the tracking system 12, in the manner described above. In operation, after the c-arm halves 72 and rails 74 are connected, the computer 50 (FIG. 1) controls the motors 79, 81 to move the source 22 and detector 24 about the x-axis. Although an effort is made to keep the source 22 and detector 24 180 degrees apart, the carriages 78, 80 are independent, so precision will not be achieved. As described above, the locators 40 and the tracking system 12 (FIG. 1) can be used to match each x-ray image with the actual locations of the source 22 and detector 24 and either "correct" for the location or otherwise take into account the actual locations of the source 22 and detector 24 when reconstructing the 3D image. As in the embodiments above, the c-arm halves 72 and bases 76 are moved along the x-axis as controlled by the computer 50.

Other variations of the present invention include a c-arm having three or more c-arm sections that are slidably mounted relative to one another, or three or more c-arm sections that are telescoping mounted relative to one another. This would further reduce the collapsed dimensions of the c-arm.

Alternatively, the source 32 and detector 34 can each be mounted on a four-bar linkage designed to approximate arcs. It is not necessary that the source 32 and detector 34 move along perfect circles—only that their positions be known. Computer-controlled motors or other actuators can be used to move the source 32 and detector 34 along the arcs while taking images at known positions and orientations. The positions and orientations of the source and detector are also determined by the tracking system such that the images can be corrected based upon the actual positions of the source and detector at each of the plurality of rotational positions about the patient.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope. Alphanumeric identifiers in method steps are for the purpose of ease of reference in dependent claims and are not intended to signify a required sequence of performance, and unless otherwise explicitly stated, such sequence should not be inferred.

What is claimed is:

1. An imaging system comprising:
    a first arm section;
    a second arm section;
    an x-ray source mounted to the first arm section;
    an x-ray detector mounted to the second arm section;
    the first arm section and the x-ray source movable relative to the second arm section and the x-ray detector between an extended position and a collapsed position, wherein the first arm section and the second arm section are slidably mounted relative to one another, wherein the first arm section is arcuate and the second arm section is arcuate and wherein the first arm section and the second arm section are rotatable about an axis generally perpendicular to a plane of the first arm section and the second arm section; and
    a carriage, to which the first arm section and the second arm section are slidably mounted, positioned below a patient support surface and wherein the source and detector are positioned below the patient support surface when the first arm section and the second arm section are in the collapsed position.

2. The imaging system of claim 1 wherein the first arm section and the second arm section are slidable relative to one another to form a c-arm having the x-ray source mounted proximate a first end of the c-arm and the x-ray detector mounted proximate a second end of the c-arm.

3. The imaging system of claim 2 wherein the c-arm is mounted to the carriage such that the c-arm is rotatable generally about an area interior of an arc of the c-arm.

4. The imaging system of claim 3 wherein the c-arm is rotatable generally about an axis between the first end and the second end of the c-arm.

5. The imaging system of claim 3 wherein one of the first arm section and the second arm section is slidable at least partially within the other of the first arm section and the second arm section.

6. The imaging system of claim 1 further including a tracking system determining a position of the detector.

7. The imaging system of claim 6 wherein the detector is movable about a generally arcuate path and wherein the detector takes an x-ray image at each of a plurality of positions spaced about the arcuate path, the system further including a computer correlating the positions of the detector as determined by the tracking system with each x-ray image, the computer reconstructing a 3D image based upon the plurality of x-ray images and the correlated positions of the detector.

8. The imaging system of claim 7 wherein the tracking system further tracks the positions of the source as the source moves along a source path, and wherein the reconstructs the 3D image based upon the positions of the source when each of the plurality of x-ray images was taken.

9. The imaging system of claim 7 wherein the tracking system optically determines the positions of the detector.

10. A method of operating an imaging system including the steps of:
    a) rotating an x-ray source and an x-ray detector at least partially about a patient support surface;
    b) during said step a), generating an x-ray image from each of a plurality of rotational positions about the patient support surface;
    c) after said step b), moving the x-ray source to a stored position under a patient support surface; and
    d) after said step b), moving the x-ray detector to a stored position under the patient support surface;
    wherein the x-ray source and the x-ray detector are mounted proximate opposite ends of a c-arm during said step a) and wherein said steps b) and c) include the step of moving the x-ray source and the x-ray detector toward one another along the c-arm.

11. The method of claim 10 wherein the x-ray source is mounted proximate an end of an arcuate first c-arm section and the x-ray detector is mounted proximate an end of an arcuate second c-arm section.

12. The method of claim 11 wherein the first and second c-arm sections are slidably mounted relative to one another.

13. The method of claim 12 wherein one of the first and second c-arm sections is telescopically mounted within the other of the first and second c-arm sections.

14. The method of claim 10 wherein the x-ray source is mounted proximate an end of a first arm and the x-ray source is mounted proximate an end of a second arm, the first and second arms mounted to a base beneath the patient support surface.

* * * * *